US010518080B2

(12) United States Patent
Alexander et al.

(10) Patent No.: US 10,518,080 B2
(45) Date of Patent: Dec. 31, 2019

(54) MOTION SICKNESS MITIGATION DEVICE

(71) Applicant: GM Global Technology Operations LLC, Detroit, MI (US)

(72) Inventors: Paul W. Alexander, Ypsilanti, MI (US); Olivia Stoneman, Shelby Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 157 days.

(21) Appl. No.: 15/854,249

(22) Filed: Dec. 26, 2017

(65) Prior Publication Data
US 2019/0192846 A1 Jun. 27, 2019

(51) Int. Cl.
*A61N 1/04* (2006.01)
*A61N 1/36* (2006.01)
*D02G 3/44* (2006.01)
*D04B 1/14* (2006.01)
*D04B 1/22* (2006.01)

(52) U.S. Cl.
CPC ......... *A61N 1/0472* (2013.01); *A61N 1/3603* (2017.08); *D02G 3/446* (2013.01); *D04B 1/14* (2013.01); *D04B 1/22* (2013.01); *D10B 2401/021* (2013.01); *D10B 2401/022* (2013.01); *D10B 2401/18* (2013.01); *D10B 2505/08* (2013.01); *D10B 2505/12* (2013.01)

(58) Field of Classification Search
CPC . D02G 3/446; D04B 1/14; D04B 1/22; D10B 2401/021; D10B 2401/18; D10B 2505/08; D10B 2505/12
See application file for complete search history.

(56) References Cited

U.S. PATENT DOCUMENTS

| | | | |
|---|---|---|---|
| 5,021,281 A | 6/1991 | Bompard et al. | |
| 5,858,159 A | 1/1999 | Holbrook et al. | |
| 6,350,709 B1 | 2/2002 | Veiga | |
| 6,704,603 B1 * | 3/2004 | Gesotti | A61N 1/36003 607/62 |
| 6,808,587 B2 | 10/2004 | Bohm et al. | |

(Continued)

OTHER PUBLICATIONS

U.S. Appl. No. 16/161,241, filed Oct. 16, 2018.
(Continued)

*Primary Examiner* — Paula J Stice
(74) *Attorney, Agent, or Firm* — Quinn IP Law

(57) ABSTRACT

A motion sickness mitigation device includes a textile material having a first surface, a second surface disposed opposite the first surface, and a first raised portion extending from the first surface and configured for contacting a skin of a user. The textile material defines a first pocket and a second pocket therein between the first surface and the second surface, and the second pocket is spaced apart from the first pocket. The device further includes a controller disposed within the first pocket and configured for transmitting an electrical signal. The device also includes a first electrical excitation pad disposed within the second pocket, covered by the first raised portion, and disposed in electrical communication with the controller. The first electrical excitation pad is configured for receiving the electrical signal and electrically stimulating the skin of the user through the textile material to thereby mitigate motion sickness.

18 Claims, 1 Drawing Sheet

(56) References Cited

U.S. PATENT DOCUMENTS

| | | | |
|---|---|---|---|
| 8,362,882 B2 | 1/2013 | Heubel et al. | |
| 8,550,222 B2 | 10/2013 | Browne et al. | |
| 9,521,885 B2 | 12/2016 | Weber et al. | |
| 2006/0186700 A1 | 8/2006 | Browne et al. | |
| 2006/0211934 A1* | 9/2006 | Hassonjee | A61B 5/0245 600/372 |
| 2008/0143080 A1* | 6/2008 | Burr | D04B 1/14 280/495 |
| 2010/0129575 A1 | 5/2010 | Veiga | |
| 2011/0062134 A1 | 3/2011 | Lochtman et al. | |
| 2012/0280479 A1 | 11/2012 | Barth et al. | |
| 2016/0303799 A1 | 10/2016 | Pettey et al. | |
| 2017/0249033 A1 | 8/2017 | Podhajny et al. | |
| 2017/0319844 A1* | 11/2017 | Woo | A61N 1/04 |
| 2018/0344969 A1 | 12/2018 | Stoneman et al. | |

OTHER PUBLICATIONS

Electrical Stimulation for Nausea, Vomiting and Motion Sickness (PrimaBella and ReliefBand) and Other Selected Indications, Sep. 13, 2018, pp. 1-18, Website: http://www.aetna.com/cpb/medical/data/600_699/0676.html.

International Neuromodulation Society, About Neuromodulation, Sep. 13, 2018, pp. 1-3, website: https://www.neuromodulation.com/about-neuromodulation.

Anna Lee and Lawrence Ty Fan, Stimulation of the wrist acupuncture point P6 for preventing postoperative nausea and vomiting (NIH-PA Author Manuscript), Apr. 15, 2009 (published on-line), 1-64, HHS Public Access, USA (https://www.ncbi.nlm.nih.gov/pmc/articles/PMC3113464).

Lee MY and Min HS, Effects of the Nei-Guan acupressure by wrist band on postoperative nausea and vomiting after middle ear surgery (PubMed.gov), Aug. 2008, 1-2, NCBI, Korea, USA (https://www.ncbi.nlm.nih.gov/pubmed/18753802).

Hewitt V and Watts R., The effectiveness of non-invasive complementary therapies in reducing postoperative nausea and vomiting following abdominal laparoscopic surgery in women: a systematic review (PubMed.gov), 2009, 1-3, NCBI, Australia, USA (https://www.ncbi.nlm.nih.gov/pubmed/27819924).

White PF, Issioui T, Jones SB, Coleman JE, Waddle JP, Markowitz SD, Coloma M, Macaluso AR, Ing CH, Comparative efficacy of acustimulation (ReliefBand) versus ondansetron (Zofran) in combination with droperidol for preventing nausea and vomiting (PubMed.gov), Nov. 2002, 1-2, NCBI, USA (https://www.ncbi.nlm.nih.gov/pubmed/12411789).

Lee A and Fan LT, Stimulation of the wrist acupuncture point P6 for preventing postoperative nausea and vomiting (PubMed.gov), Apr. 15, 2009, 1-3, NCBI, USA (https://www.ncbi.nlm.nih.gov/pubmed/19370583).

Ming JL, Kuo BI, Lin JG, Lin LC, The efficacy of acupressure to prevent nausea and vomiting in post-operative patients (PubMed.gov), Aug. 2002, 1-2, NCBI, Taiwan, USA (https://www.ncbi.nlm.nih.gov/pubmed/12139646).

Lee A and Fan LT, Table 1: Estimated NNT for preventing PONV (P6 acupoint stimulation versus sham), Apr. 15, 2009 (published on-line), 1-64, HHS Public Access, USA (https://www.ncbi.nlm.nih.gov/pmc/articles/PMC3113464).

* cited by examiner

MOTION SICKNESS MITIGATION DEVICE

INTRODUCTION

The disclosure relates to a motion sickness mitigation device.

Motion sickness is a condition in which a disagreement exists between visually perceived movement and a vestibular system's sense of movement. Depending on the cause, motion sickness can also be referred to as seasickness, car sickness, simulation sickness, or airsickness. Motion sickness is a fairly common condition, with some reports estimating that nearly one in four people have experienced motion sickness while in a device or vehicle. Further, research indicates that people are nearly twice as likely to experience motion sickness while traveling in an autonomous vehicle as compared to traveling in a human-operated vehicle.

SUMMARY

A motion sickness mitigation device includes a textile material having a first surface, a second surface disposed opposite the first surface, and a first raised portion extending from the first surface and configured for contacting a skin of a user. The textile material defines a first pocket and a second pocket therein between the first surface and the second surface, and the second pocket is spaced apart from the first pocket. The motion sickness mitigation device further includes a controller configured for transmitting an electrical signal. The motion sickness mitigation device also includes a first electrical excitation pad disposed within the second pocket, covered by the first raised portion, and disposed in electrical communication with the controller. The first electrical excitation pad is configured for receiving the electrical signal and electrically stimulating the skin of the user through the textile material to thereby mitigate motion sickness.

In one aspect, the first surface may include a locating graphic configured for aligning the skin of the user with the first electrical excitation pad.

In another aspect, the textile material may define a third pocket therein between the first surface and the second surface, wherein the third pocket is spaced apart from the second pocket. The textile material may also have a second raised portion extending from the first surface and spaced apart from the first raised portion. In addition, the motion sickness mitigation device may include an activation switch disposed within the third pocket and covered by the second raised portion, wherein the activation switch is configured for actuating the first electrical excitation pad. The activation switch may be selectively actuatable on demand.

In another aspect, the textile material may further define a fourth pocket therein between the first surface and the second surface, wherein the fourth pocket is disposed between the second pocket and the third pocket. The textile material may have a third raised portion extending from the first surface, disposed between the first raised portion and the second raised portion, and configured for contacting the skin of the user. The motion sickness mitigation device may include a second electrical excitation pad disposed within the fourth pocket, covered by the third raised portion, and disposed in electrical communication with the controller. The second electrical excitation pad is configured for receiving the electrical signal and electrically stimulating the skin of the user through the textile material at the third raised portion to thereby mitigate motion sickness.

In a further aspect, the motion sickness mitigation device may include a first plurality of wires inlaid in the textile material and configured for transmitting the electrical signal between at least two of the controller, the first electrical excitation pad, the second electrical excitation pad, and the activation switch.

In one aspect, the motion sickness mitigation device may include a conduit disposed between the first surface and the second surface and configured for delivering a gel to at least the first raised portion.

In another aspect, the motion sickness mitigation device may include an indicator inlaid in the textile material and configured for conveying an electrical excitation level to the user. The motion sickness mitigation device may also include a second plurality of wires inlaid in the textile material and configured to transmit the electrical signal between at least two of the indicator, the activation switch, and the controller.

In a further aspect, the motion sickness mitigation device may include an inflatable tube disposed between the first surface and the second surface. The inflatable tube may be selectively inflatable to thereby raise a section of the textile material from the first surface and present the section to the user.

In one embodiment, a motion sickness mitigation device includes a knitted fabric formed from at least one yarn and including a plurality of interlocking loops. The knitted fabric has a first surface and a second surface disposed opposite the first surface. The knitted fabric has a first raised portion, a second raised portion, and a third raised portion each extending from the first surface and configured for contacting the skin of a user. The second raised portion is spaced apart from the first raised portion, and the third raised portion is disposed between the first raised portion and the second raised portion. The knitted fabric defines a first pocket, a second pocket, a third pocket, and a fourth pocket therein between the first surface and the second surface. The second pocket is disposed between the first pocket and the third pocket, and the fourth pocket is disposed between the second pocket and the third pocket. The motion sickness mitigation device also includes a controller disposed within the first pocket and configured for transmitting an electrical signal. In addition, the motion sickness mitigation device includes a first electrical excitation pad disposed within the second pocket, covered by the first raised portion, and disposed in electrical communication with the controller. Further, the motion sickness mitigation device includes a second electrical excitation pad disposed within the fourth pocket, covered by the third raised portion, and disposed in electrical communication with the controller. The motion sickness mitigation device also includes an activation switch and a locating graphic shaped as a hand. The locating graphic is disposed between the second raised portion and the third raised portion and is configured for aligning the skin of the user with the first electrical excitation pad and the second electrical excitation pad. The activation switch is disposed within the third pocket, covered by the second raised portion, and is configured for actuating the first electrical excitation pad and the second electrical excitation pad. The first electrical excitation pad and the second electrical excitation pad are configured for receiving the electrical signal and electrically stimulating the skin of the user through the knitted fabric to thereby mitigate motion sickness.

In one aspect, the motion sickness mitigation device may further include an indicator having a plurality of light emitting diodes and inlaid in the knitted fabric. The plurality of light emitting diodes may be configured for conveying an electrical excitation level to the user.

The at least one yarn may be hygroscopic. In another aspect, the at least one yarn may be hydrophilic. In a further aspect, the at least one yarn may be hydrophobic.

In another aspect, the motion sickness mitigation device may include an armrest configured to support a wrist of the user, and the knitted fabric may be disposed on the armrest. The first raised portion and the second raised portion may be arranged as a plurality of ribs spaced apart from one another and may be alignable with the wrist of the user.

In one aspect, the motion sickness mitigation device may further include a first plurality of wires inlaid in the knitted fabric and configured for transmitting the electrical signal between at least two of the controller, the first electrical excitation pad, the second electrical excitation pad, and the activation switch. The activation switch may be selectively actuatable on demand.

In another embodiment, a motion sickness mitigation device includes a textile material having a first surface, a second surface disposed opposite the first surface, and a first raised portion extending from the first surface and configured for contacting a skin of a user. The textile material is formed from a first yarn and includes a plurality of interlocking loops. The motion sickness mitigation device also includes a second yarn inlaid in the textile material and arranged to form at least a first electrical excitation pad configured for receiving the electrical signal and electrically stimulating the skin of the user through the textile material to thereby mitigate motion sickness.

In one aspect, the second yarn may be inlaid in the textile material and also arranged to form at least one of an activation switch inlaid in the textile material and configured for activating the first electrical excitation pad; a second electrical excitation pad inlaid in the textile material and configured for receiving the electrical signal and electrically stimulating the skin of the user through the textile material to thereby mitigate motion sickness; and an indicator inlaid in the textile material and configured for conveying an electrical excitation level to the user.

DETAILED DESCRIPTION

Figure 1:
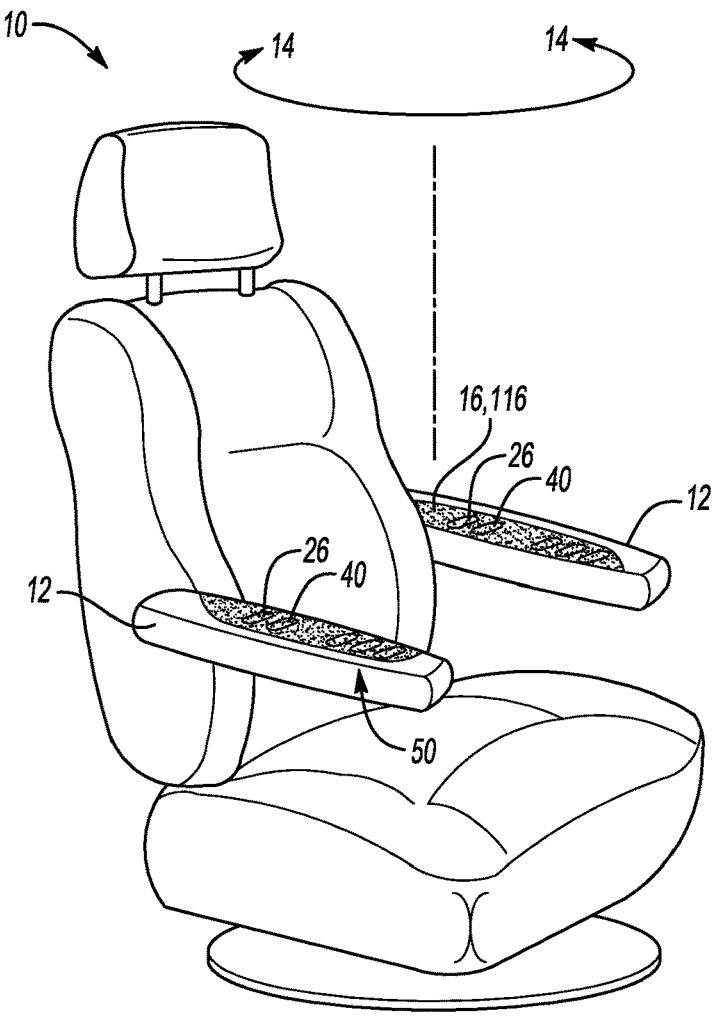
FIG. 1 is a schematic illustration of a perspective view of a seat that includes a motion sickness mitigation device.
Figure 2:
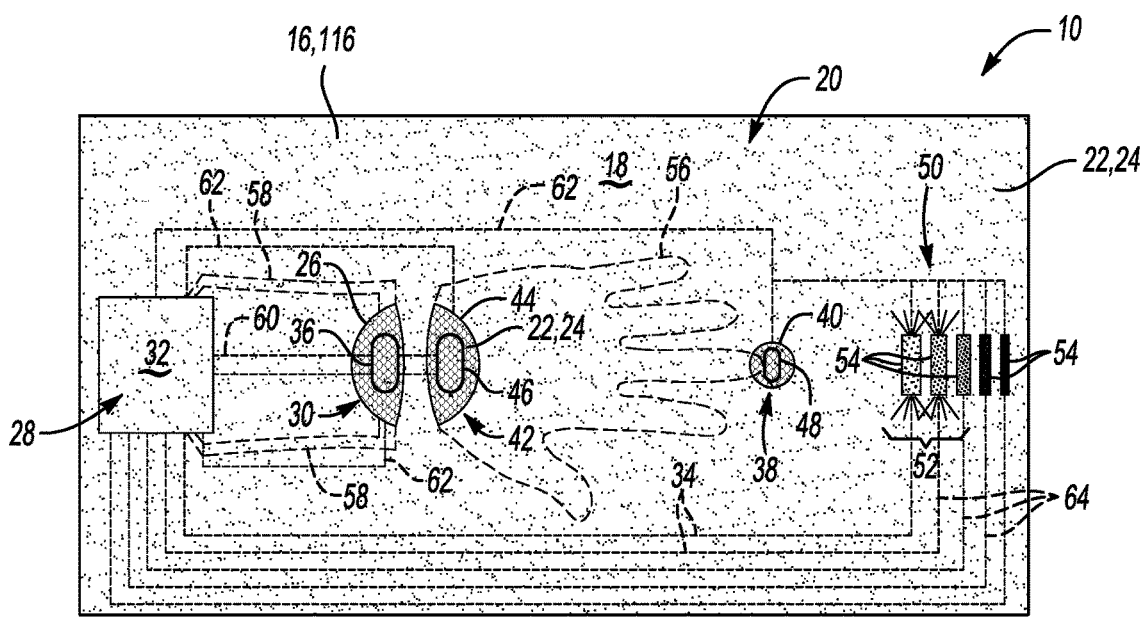
FIG. 2 is a schematic illustration of a top view of the motion sickness mitigation device of FIG. 1.

Referring to the Figures, wherein like reference numerals refer to like elements, a motion sickness mitigation device 10 is shown generally in FIGS. 1 and 2. The motion sickness mitigation device 10 may be useful for applications and components that are operable under conditions in which a user may experience motion sickness due to conflicting messages generated by the user's sensory system. That is, the motion sickness mitigation device 10 may minimize or eliminate symptoms of motion sickness, e.g., nausea, dizziness, increased body temperature, sweating, discomfort, and the like, for the user. As such, the motion sickness mitigation device 10 may be useful for vehicular applications such as, but not limited to, automobiles, airplanes, trains, trams, and boats. Alternatively, the motion sickness mitigation device 10 may be useful for non-vehicular applications such as examination chairs, theater seating, gaming chairs, stretchers, and the like. In particular, by way of a non-limiting example, the motion sickness mitigation device 10 may be useful for autonomous vehicle applications in which the user does not steer or control the motive power of the autonomous vehicle.

As described in further detail below, the motion sickness mitigation device 10 may be selectively operated by the user on an on-demand basis. That is, the user may actuate and/or control the motion sickness mitigation device 10 in advance of or upon beginning to experience symptoms of motion sickness. As shown in FIG. 1, in one embodiment, the motion sickness mitigation device 10 may be available to the user on an armrest 12 of a seat that is stationary or non-stationary. For example, the armrest 12 may be configured to support a wrist of the user and may be a component of a passenger seat of an autonomous vehicle. The passenger seat may support the user during operation of the autonomous vehicle and may be configured to swivel or pivot (as illustrated by arrows 14), translate fore and aft, and/or change locations within the autonomous vehicle.

Referring now to FIG. 2, the motion sickness mitigation device 10 includes a textile material 16 having a first surface 18 and a second surface 20 disposed opposite the first surface 18. The textile material 16 may be a generally soft and flexible material that is supportive and comfortable for the wrist, a hand, and/or a forearm of the user to rest upon.

More specifically, the term "textile material 16" as used herein refers to a material which is formed by one or more of weaving, knitting, crocheting, braiding, or a combination of these to form the textile material 16, and where weaving generates a woven structure in the textile material 16, knitting generates a knitted structure in the textile material 16, crocheting generates a crocheted structure in the textile material 16, and braiding generates a braided structure in the textile material 16. The textile material 16 made using a combination of these methods could have portions of the textile material 16 which incorporate multiple structures. For example, a knitted portion could be formed using braided fibers, fibers could be woven through a knitted or crocheted structure to provide dimensional strength and/or stabilization, a crocheted edge could be formed on a knitted or woven structure, woven layers could be knitted together to form a multi-layer textile material 16 such as a 3D textile material 16, etc.

The textile material 16 can include one or more types of fiber, including one or more of an organic fiber such as an animal fiber, a plant-based fiber, a synthetic fiber such as a polymeric fiber, a carbon-based fiber, a ceramic-based fiber such as a glass-based fiber, a metal-based fiber including steel-based fiber and/or wire and aluminum-based fiber and/or wire, a blended fiber such as an animal/synthetic blended fiber, an animal/plant blended fiber, a plant/synthetic blended fiber, a glass/polymer blended fiber (fiberglass), a metal/synthetic blended fiber, etc., and/or a combination of two or more of the various fiber types. Animal fiber can include wool fiber produced from the hair and/or fur of any animal providing hair/fur suitable for fiber production, including by way of non-limiting example, sheep, goats, rabbits, llamas, etc., silk fiber produced from insect cocoons, and the like. Plant-based fiber can include fiber produced from any plant providing a plant material which is suitable for fiber production, including by way of non-limiting example, cotton, flax, wood (acetate, rayon), bamboo, jute, hemp, raffia, sisal, soy, etc. Synthetic fiber can include, by way of non-limiting example, fibers made of one or more of acrylic, Kevlar®, nylon, Nomex®, polyester, spandex, and the like. The fiber can be formed, by way of non-limiting example, by spinning, extrusion, drawing, and the like. The textile material 16 can be formed of a yarn 22 (FIG. 2) including a plurality of fibers which have been spun or twisted together or otherwise interlocked or joined to form the yarn 22. The textile material 16 can include monofilament fiber, polyfilament fiber, staple fiber, or a combination of these.

The textile material 16 can be formed as a multi-dimensional and/or multi-layer material, such as a 2D material, a 3D material, a multi-layer mesh material, a multi-layer woven material, and the like. The textile material 16 can be formed using a combination of techniques. For example, the textile material 16 can be a knitted 3D material into which weft and/or warp threads have been woven to provide for directional properties such as directional stretch ability, predetermined distortion of spaces in the textile structure under load, damping characteristics, etc., where the examples shown are not intended to be limiting. The textile material 16 can include multiple layers formed by the same technique, such as a double-layer weave material, or where at least one of the multiple layers is formed by a different technique than another of the multiple layers.

Further, the textile material 16 described herein is formed by one or more of weaving, knitting, crocheting, braiding, and the like such that the fibers are spaced from one another and can move relative to each other, for example, under load, such that spacing between the fibers and the orientation of one fiber to another changes in dimension, shape, and orientation in response to a change in the direction and magnitude or the load being imposed on the textile material 16. As such, the textile material 16 can be characterized as one or more of elastic, stretchable, porous, and conductive and capable of providing a response which can include one or more of a stiffness response, an energy dissipation response, and a thermal response.

The textile material 16, due to the porous structure provided by the spacing between fibers forming the textile material 16, may provide for fluid flow (heat, air, and vapor including water vapor) through the textile material 16, where the rate and capacity of the fluid flow and diffusivity of the textile material 16 can change as an applied load varies. Further, the response characteristics of the textile material 16 can be varied by varying one or more of a stitch type, a stitch pattern, a yarn type, a yarn denier, a needle size, a fiber type, a fiber size, a stitch density, a warp pattern, a weft pattern, a weave type, a braiding pattern, etc. of the textile material 16, where these features of the textile material 16 may determine characteristics of the textile material 16 including, by way of example, the density, thickness, porosity, conductivity, elasticity, etc., of the textile material 16, and the shape, size, orientation, and dynamic response of spaces defined between the fibers in the textile material 16.

In one embodiment as described with reference to FIG. 2, the textile material 16 is a knitted fabric 116 formed from at least one yarn 22 and including a plurality of interlocking loops 24. For this embodiment, the knitted fabric 116 is disposed on the armrest 12 and has the first surface 18 and the second surface 20 disposed opposite the first surface 18. In one example, the at least one yarn 22 may be hygroscopic. In another example, the at least one yarn 22 may be hydrophilic. In yet another example, the at least one yarn 22 may be hydrophobic. In a further example, the at least one yarn 22 may be a combination of hygroscopic, hydrophilic, and/or hydrophobic. That is, depending on the application of the motion sickness mitigation device 10, the textile material 16 may reject water, may attract water so as to wick moisture away from a skin of the user, and/or may absorb water from an environment surrounding the motion sickness mitigation device 10.

The textile material 16 also includes a first raised portion 26 extending from the first surface 18 and configured for contacting the skin of the user. That is, the first raised portion 26 may be operable to support, massage, stimulate, and/or contact the skin of the user. For example, the first raised portion 26 may be arranged as a rib, band, circular area, and the like.

As described with continued reference to FIG. 2, the textile material 16 also defines a first pocket 28 and a second pocket 30 therein between the first surface 18 and the second surface 20. That is, the first pocket 28 and the second pocket 30 may be an enclosed gap between the first surface 18 and the second surface 20. The second pocket 30 is spaced apart from the first pocket 28, and the second pocket 30 may be covered by the first raised portion 26.

The motion sickness mitigation device 10 further includes a controller 32 configured for transmitting an electrical signal (represented generally at 34 in FIG. 2). In one example, the controller 32 may be disposed within the first pocket 28. In another example, the controller 32 may be formed from a yarn 22 and inlaid in the textile material 16. In yet another example, the controller 32 may be located apart from the textile material 16, i.e., spaced remotely from the textile material 16. That is, for automotive applications, the controller 32 may be located in another portion of the vehicle. The controller 32 may include suitable logic to control operation of the motion sickness mitigation device 10 based on actuation by the user. Although not shown, the controller 32 may additionally include one or more central processing units or processors, a network interface, memory, and/or bulk storage.

In addition, referring again to FIG. 2, the motion sickness mitigation device 10 includes a first electrical excitation pad 36 disposed within the second pocket 30, covered by the first raised portion 26, and disposed in electrical communication with the controller 32. The first electrical excitation pad 36 is configured for receiving the electrical signal 34 and electrically stimulating the skin of the user through the textile material 16 to thereby mitigate motion sickness for the user. In particular, the first electrical excitation pad 36 may generate electrical stimulation pulses to, for example, a ventral side of the wrist of the user.

In one example, the first electrical excitation pad 36 may include an electro-acupuncture device. In another example, the first electrical excitation pad 36 may include a pulse generator and one or more electrodes. The pulse generator, which may be powered by any suitable energy source, such as a vehicle battery or a battery disposed within the first pocket 28, may provide electrical stimulation pulses to the one or more electrodes. In operation, the first electrical excitation pad 36 may transfer the electrical stimulation pulses to the skin of the user through the textile material 16 and thereby provide motion sickness mitigation therapy.

The textile material 16 may further define a third pocket 38 therein between the first surface 18 and the second surface 20 and spaced apart from the second pocket 30. In particular, the second pocket 30 may be disposed between the first pocket 28 and the third pocket 38. That is, the third pocket 38 may be an enclosed gap between the first surface 18 and the second surface 20. The textile material 16 may also include a second raised portion 40 extending from the first surface 18 and spaced apart from the first raised portion 26. The second raised portion 40 may cover the third pocket 38.

As described with continued reference to FIG. 2, the textile material 16 may further define a fourth pocket 42 therein between the first surface 18 and the second surface 20, and disposed between the second pocket 30 and the third pocket 38. That is, the fourth pocket 42 may be an enclosed gap between the first surface 18 and the second surface 20.

The textile material 16 may also have a third raised portion 44 extending from the first surface 18, disposed between the first raised portion 26 and the second raised portion 40, and configured for contacting the skin of the user. That is, the second raised portion 40 may be operable to support, massage, stimulate, and/or contact the skin of the user. For example, the second raised portion 40 may be arranged as a rib, band, circular area, and the like. In one example, the first raised portion 26 and the second raised portion 40 may be arranged as a plurality of ribs spaced apart from one another and may be alignable with the wrist of the user.

In addition, the motion sickness mitigation device 10 may include a second electrical excitation pad 46 disposed within the fourth pocket 42, covered by the third raised portion 44, and disposed in electrical communication with the controller 32. The second electrical excitation pad 46 may also be configured for receiving the electrical signal 34 and electrically stimulating the skin of the user through the textile material 16 at the third raised portion 44 to thereby mitigate motion sickness. That is, similar to the first electrical excitation pad 36, the second electrical excitation pad 46 may also generate electrical stimulation pulses to, for example, the ventral side of the wrist of the user.

In one example, the second electrical excitation pad 46 may include the electro-acupuncture device. In another example, the second electrical excitation pad 46 may include a pulse generator and one or more electrodes. In operation, the second electrical excitation pad 46 may transfer the electrical stimulation pulses to the skin of the user and thereby provide motion sickness mitigation therapy in combination with the electrical stimulation pulses transferred by the first electrical excitation pad 36. In some examples, the first electrical excitation pad 36 and the second electrical excitation pad 46 may each have a semicircular or half-moon shape. In other examples, the first electrical excitation pad 36 and the second electrical excitation pad 46 may each have a rectangular or rib shape.

As shown in FIG. 2, the motion sickness mitigation device 10 may further include an activation switch 48 disposed within the third pocket 38 and covered by the second raised portion 40, wherein the activation switch 48 is configured for actuating the first electrical excitation pad 36 and/or the second electrical excitation pad 46. That is, during operation, the user may depress the activation switch 48 to send the electrical signal 34 to the first electrical excitation pad 36 and/or the second electrical excitation pad 46. Therefore, the activation switch 48 may be selectively actuatable on demand.

In some examples, the activation switch 48 may also function as an intensity and/or frequency adjustment control. For example, the user may depress the activation switch 48 once to initially actuate the first electrical excitation pad 36 and/or the second electrical excitation pad 46. The user may then subsequently depress the activation switch 48 to increase an intensity and/or frequency of the electrical stimulation provided by the first and/or second electrical excitation pads 36, 46. Finally, if desired, the user may depress the activation switch again to decrease the intensity and/or frequency of the electrical stimulation and thereby modulate the electrical stimulation according to a severity of the motion sickness symptoms. In one example, the activation switch 48 may include a micro switch configured to detect pressure applied to the third raised portion 44 and/or the activation switch 48 and adjust the intensity and/or frequency of the electrical signal 34 based on the detected pressure.

Referring again to FIG. 2, the motion sickness mitigation device 10 may further include an indicator 50 inlaid in the textile material 16 and configured for conveying an electrical excitation level 52 to the user. For example, the indicator 50 may include a plurality of light emitting diodes 54 configured for conveying the electrical excitation level 52 to the user. In one non-limiting example, the indicator 50 may include five light emitting diodes 54 which may respectively correspond to five distinct levels of electrical stimulation, i.e., the electrical excitation level 52, provided or available to the user. The plurality of light emitting diodes 54 may sequentially illuminate as the electrical excitation level 52 increases.

For ease of use, the first surface 18 may further include a locating graphic 56 configured for aligning the skin of the user with the first electrical excitation pad 36 and/or the second electrical excitation pad 46. For example, the locating graphic 56 may be shaped as a hand and may be disposed between the second raised portion 40 and the third raised portion 44. The locating graphic 56 may function to guide the user regarding correct placement of the skin of the user against the textile material 16 to ensure sufficient electrical stimulation for mitigating motion sickness.

Alternatively or additionally, the motion sickness mitigation device 10 may further include an inflatable tube 58 disposed between the first surface 18 and the second surface 20. The inflatable tube 58 may be selectively inflatable to thereby raise a section of the textile material 16 from the first surface 18 and present the section to the user. For example, the inflatable tube 58 may inflate upon actuation of the activation switch 48 to surround, cradle, align, or support the wrist of the user. In another example, the inflatable tube 58 may present the activation switch and/or the first and second electrical excitation pads 36, 46 to the user.

Further, to ensure that proper electrical stimulation is transmitted to the skin of the user during operation of the motion sickness mitigation device 10, the motion sickness mitigation device 10 may further include a conduit 60 disposed between the first surface 18 and the second surface 20 and configured for delivering a gel to at least the first raised portion 26, e.g., to the first raised portion 26 and the third raised portion 44. The gel may be electrically conductive, may be suitable for application to the skin of the user, and may optimize transmission of the electrical stimulation to the skin of the user.

The motion sickness mitigation device 10 may also include a first plurality of wires 62 inlaid in the textile material 16 and configured for transmitting the electrical signal 34 between at least two of the controller 32, the first electrical excitation pad 36, the second electrical excitation pad 46, and the activation switch 48. Likewise, the motion sickness mitigation device 10 may further include a second plurality of wires 64 inlaid in the textile material 16 and configured to transmit the electrical signal 34 between at least two of the indicator 50, the activation switch 48, and the controller 32.

Any of the first plurality of wires 62 and the second plurality of wires 64 may be inlaid in the textile material 16 so as to be visible to the user as a design element or feature of the motion sickness mitigation device 10, e.g., as a logo, a word, a contrasting color, and the like. Alternatively, any of the first plurality of wires 62 and the second plurality of wires 64 may be inlaid in the textile material 16 so as to be invisible or hidden to the user.

In another embodiment, the textile material 16 is formed from the at least one yarn 22, i.e., a first yarn 22, and includes the plurality of interlocking loops 24. Further, the motion sickness mitigation device 10 includes a second yarn 22 inlaid in the textile material 16 and arranged to form at least the first electrical excitation pad 36 configured for receiving the electrical signal 34 and electrically stimulating the skin of the user through the textile material 16 to thereby mitigation motion sickness. That is, the second yarn 22 may be an active yarn, e.g., may conduct electrical energy, may change shape or size in response to an actuation signal, may conduct thermal energy, may contract or expand, may tighten or slacken, may change color, etc., and may be arranged to form a stitch pattern that is the first electrical excitation pad 36. Stated differently, the second yarn 22 may respond to an external stimulus (e.g., an electrical, thermal, or magnetic activation signal) with a physical change. The second yarn 22 is inlaid or knitted into the textile material 16 between or through or around the plurality of interlocking loops 24.

In one example, the second yarn 22 may be a shape-memory alloy (SMA) filament and/or shape-memory polymer (SMP) filament that is embedded and inlaid within the textile material 16. For example, the SMA and/or SMP filament may be actuatable, e.g., via an (electric or thermal or magnetic) activation signal, to move the second yarn 22 outboard past the first yarn 22 to thereby form the first raised portion 26, the second raised portion 40, and/or the third raised portion 44. Optionally, the SMA and/or SMP filament may be a single SMA and/or SMP yarn 22 that is kitted or woven or inlaid into the textile material 16. As another option, the SMA and/or SMP filament may include multiple SMA and/or SMP threads that are woven, knitted, and/or sewn with the first yarn 22 to form the textile material 16.

Further, for any of the herein described aspects and features, the second yarn 22 may include an electroactive polymer (EAP) filament and/or an electrorheological polymer (ERP) insert that is embedded within the textile material 16. The EAP filament and/or ERP insert may be actuatable, e.g., in response to an (electric field) activation signal.

In another example, the second yarn 22 may be inlaid in the textile material 16 and also arranged to form at least one of the activation switch 48 inlaid in the textile material 16 and configured for activating the first electrical excitation pad 36; the second electrical excitation pad 46 inlaid in the textile material 16 and configured for receiving the electrical signal 34 and electrically stimulating the skin of the user through the textile material 16 to thereby mitigate motion sickness; and the indicator 50 inlaid in the textile material 16 and configured for conveying the electrical excitation level 52 to the user. The one or more of the activation switch 48, the first electrical excitation pad 36, the second electrical excitation pad 46, the indicator 50, and/or any electrical leads or connections may form a stitch pattern that is different from other areas or sections of the textile material 16 so that the user may visually distinguish the stitch pattern from a background of the textile material 16 and locate one of more of the activation switch 48, the first electrical excitation pad 36, the second electrical excitation pad 46, the indicator 50, and/or any electrical leads or connections.

Therefore, during operation, the motion sickness mitigation device 10 provides on-demand and tunable relief from the symptoms of motion sickness for the user. Further, the motion sickness mitigation device 10 is conveniently integrated into a vehicle or seat, is compact and economical, and increases user comfort during vehicle or seat operation.

While the best modes for carrying out the disclosure have been described in detail, those familiar with the art to which this disclosure relates will recognize various alternative designs and embodiments for practicing the disclosure within the scope of the appended claims.

What is claimed is:

1. A motion sickness mitigation device for a seat, the motion sickness mitigation device comprising:
   a textile material having:
      a first surface;
      a second surface disposed opposite the first surface;
      a first raised portion extending from the first surface and configured for contacting a skin of a user disposed on the seat;
      a second raised portion extending from the first surface, configured for contacting the skin of the user, and spaced apart from the first raised portion; and
      a third raised portion extending from the first surface, disposed between the first raised portion and the second raised portion, and configured for contacting the skin of the user:
   wherein the textile material defines a first pocket, a second pocket, a third pocket, and a fourth pocket therein between the first surface and the second surface, and wherein the second pocket is spaced apart from the first pocket and the third pocket, and the fourth pocket is disposed between the second pocket and the third pocket;
   a controller configured for transmitting an electrical signal;
   a first electrical excitation pad disposed within the second pocket, covered by the first raised portion, and in electrical communication with the controller, wherein the first electrical excitation pad is configured for receiving the electrical signal and electrically stimulating the skin of the user through the textile material to thereby mitigate motion sickness;
   a second electrical excitation pad disposed within the fourth pocket, covered by the third raised portion, and in electrical communication with the controller, wherein the second electrical excitation pad is configured for receiving the electrical signal and electrically stimulating the skin of the user through the textile material at the third raised portion to thereby mitigate motion sickness; and
   an activation switch disposed within the third pocket and covered by the second raised portion, wherein the activation switch is configured for actuating at least one of the first electrical excitation pad and the second electrical excitation pad.

2. The motion sickness mitigation device of claim 1, further including a first plurality of wires inlaid in the textile material and configured for transmitting the electrical signal between at least two of the controller, the first electrical excitation pad, the second electrical excitation pad, and the activation switch.

3. The motion sickness mitigation device of claim 1, wherein the activation switch is selectively actuatable on demand.

4. The motion sickness mitigation device of claim 1, further including a conduit disposed between the first surface and the second surface and configured for delivering a gel to at least the first raised portion.

5. The motion sickness mitigation device of claim 1, further including an indicator inlaid in the textile material and configured for conveying an electrical excitation level to the user.

6. The motion sickness mitigation device of claim 5, further including a second plurality of wires inlaid in the textile material and configured to transmit the electrical signal between at least two of the indicator, the activation switch, and the controller.

7. The motion sickness mitigation device of claim 1, wherein the first surface includes a locating graphic configured for aligning the skin of the user with the first electrical excitation pad.

8. The motion sickness mitigation device of claim 1, further including an inflatable tube disposed between the first surface and the second surface.

9. The motion sickness mitigation device of claim 8, wherein the inflatable tube is selectively inflatable to thereby raise a section of the textile material from the first surface and present the section to the user.

10. A motion sickness mitigation device for a seat, the motion sickness mitigation device comprising:
 a knitted fabric formed from at least one yarn and including a plurality of interlocking loops, wherein the knitted fabric has:
  a first surface;
  a second surface disposed opposite the first surface; and
  a first raised portion, a second raised portion, and a third raised portion each extending from the first surface and configured for contacting a skin of a user disposed on the seat;
   wherein the second raised portion is spaced apart from the first raised portion; and
   wherein the third raised portion is disposed between the first raised portion and the second raised portion;
  wherein the knitted fabric defines a first pocket, a second pocket, a third pocket, and a fourth pocket therein between the first surface and the second surface;
   wherein the second pocket is disposed between the first pocket and the third pocket; and
   wherein the fourth pocket is disposed between the second pocket and the third pocket;
 a controller disposed within the first pocket and configured for transmitting an electrical signal;
 a first electrical excitation pad disposed within the second pocket, covered by the first raised portion, and in electrical communication with the controller;
 a second electrical excitation pad disposed within the fourth pocket, covered by the third raised portion, and in electrical communication with the controller;
 a locating graphic shaped as a hand and disposed between the second raised portion and the third raised portion, wherein the locating graphic is configured for aligning the skin of the user with the first electrical excitation pad and the second electrical excitation pad; and
 an activation switch disposed within the third pocket and covered by the second raised portion, wherein the activation switch is configured for actuating the first electrical excitation pad and the second electrical excitation pad;
  wherein the first electrical excitation pad and the second electrical excitation pad are configured for receiving the electrical signal and electrically stimulating the skin of the user through the knitted fabric to thereby mitigate motion sickness.

11. The motion sickness mitigation device of claim 10, further including an indicator having a plurality of light emitting diodes and inlaid in the knitted fabric, wherein the plurality of light emitting diodes are configured for conveying an electrical excitation level to the user.

12. The motion sickness mitigation device of claim 10, wherein the at least one yarn is hygroscopic.

13. The motion sickness mitigation device of claim 10, wherein the at least one yarn is hydrophilic.

14. The motion sickness mitigation device of claim 10, wherein the at least one yarn is hydrophobic.

15. The motion sickness mitigation device of claim 10, further comprising an armrest configured to support a wrist of the user, wherein the knitted fabric is disposed on the armrest.

16. The motion sickness mitigation device of claim 15, wherein the first raised portion and the second raised portion are arranged as a plurality of ribs spaced apart from one another and are alignable with the wrist of the user.

17. A motion sickness mitigation device for a seat, the motion sickness mitigation device comprising:
 a textile material having:
  a first surface;
  a second surface disposed opposite the first surface;
  a first raised portion extending from the first surface and configured for contacting a skin of a user disposed on the seat;
  a second raised portion extending from the first surface, configured for contacting the skin of the user, and spaced apart from the first raised portion; and
  a third raised portion extending from the first surface, disposed between the first raised portion and the second raised portion, and configured for contacting the skin of the user;
 wherein the textile material is formed from a first yarn and includes a plurality of interlocking loops;
 a controller configured for transmitting an electrical signal;
 a second yarn inlaid in the textile material and arranged to form at least:
  a first electrical excitation pad at the first raised portion, wherein the first electrical excitation pad is in electrical communication with the controller and configured for receiving the electrical signal and electrically stimulating the skin of the user through the textile material at the first raised portion to thereby mitigate motion sickness; and
  a second electrical excitation pad at the third raised portion, wherein the second electrical excitation pad is in electrical communication with the controller and configured for receiving the electrical signal and electrically stimulating the skin of the user through the textile material at the third raised portion to thereby mitigate motion sickness; and
 an activation switch inlaid in the textile material at the second raised portion and configured for actuating at least one of the first electrical excitation pad and the second electrical excitation pad.

18. The motion sickness mitigation device of claim 17, wherein the second yarn is inlaid in the textile material and also arranged to form an indicator inlaid in the textile material and configured for conveying an electrical excitation level to the user.

* * * * *